United States Patent [19]
Woodward et al.

[11] Patent Number: 5,521,183
[45] Date of Patent: May 28, 1996

[54] USE OF 5-HT LIGANDS AS ANTI-PRURITIC AGENTS

[75] Inventors: David F. Woodward; Amelia L. Nieves, both of Lake Forest, Calif.

[73] Assignee: Allergan, Waco, Tex.

[21] Appl. No.: 298,245

[22] Filed: Aug. 30, 1994

[51] Int. Cl.$^6$ .................. A61K 31/495; A61K 31/50; A61K 31/505; A61K 31/44; A61K 31/405; A61K 31/135
[52] U.S. Cl. .................. 514/250; 514/254; 514/259; 514/278; 514/304; 514/415; 514/657
[58] Field of Search .................. 514/415, 278, 514/259, 254, 304, 657, 250

[56] References Cited

PUBLICATIONS

Schworer et al., *Medline Abstracts*, abstract No. 94034099, 1993.
Herndon, Jr., J. H., Int. J. Derm., 14, 465–484 (1975), "Itching: The Pathophysiology of Pruritus".
Winkelmann, R. K., Med. Clins. N. Am., 66, 1119–1133 (1982), "Pharmacologic Control of Pruritis".
Cormia, F. E., J. Invest. Derm., 19, 21–34 (1952), "Experimental Histamine Pruritus I. Influence of Physical and Psychological Factors on Threshold Reactivity".
Wahlgren, C. F., Allergy, 47, 65–75 (1992), "Pathophysiology of itching in urticaria and atopic dermatitis".
Torebjörk & Ochoa, Soc. Neurosci. Abstr., 77.5, 228 (1981), "Pain and Itch from C Fiber Stimulation".
Hylden et al, Brain Research, 217, 212–215 (1981), "Intrathecal substance P elicits a caudally-directed biting and scratching behavior in mice".
Hylden et al, The Journal of Pharmacology and Experimental Therapeutics, 226(2), 398–404, (1983), "Pharmacological Characterization of Substance P–Induced Nociceptinin Mice: Modulation by Opiod and Noradrenergic Agonists at the Spinal Level[1]".
Meisenberg et al, Peptides, 7, 557–561 (1986), "Behavioral Alterations Induced by Substance P, Bombesin, and Related Peptides in Mice[1]".
Alhaider et al, Eur. J. Pharmacol, 249(2),151–160 (1993), "Intrathecal 5–methoxy–N,N–dimethyltryptamine in mice modulates 5–$HT_1$ and 5–$HT_3$ receptors".
Berendsen et al, Eur. J. Pharmacol., 194,201–208(1991), "A peripheral 5–$HT_{1D}$–like receptor involved in serotonergic induced hindlimb scratching in rats".
Humphrey et al, TiPS, 14(Jun.), 233–236 (1993) "A proposed new nomenclature for 5–HT receptors".
Middlemiss et al, Neurosciences and Biobehavioral Reviews, 16, 75–82(1992), "Centrally Active 5-HT Receptor Agonists and Antagonists".
Hen, R., TiPS, 13(Apr.), 160–165 (1992), "Of mice and flies: commonalities among 5–HT receptors".
Cormia et al, J. of Invest. Derm., 28 (1957), 425–433, "Proteolytic Activity in Dermatoses:Preliminary Observations on Inflammation and Pruritus".

*Primary Examiner*—Marianne M. Cintins
*Assistant Examiner*—William R. A. Jarvis
*Attorney, Agent, or Firm*—James M. Hoch; Robert J. Baran; Martin A. Voet

[57] ABSTRACT

The present invention is based on the finding that 5-HT receptor ligands are useful in treating experimental models of clinically encountered pruritus (itch). A 5-HT ligand as used in this specification is a compound capable of binding with some selectivity to one or more of the 5-HT receptor sites. Systemic administration of 5-HT agonists and antagonists causes a reduction in the number of itch-scratch responses to an ocular challenge by allergenic antigens. Therefore, the present invention relates to a method for treating pruritus by administering systemically a therapeutically effective amount of a 5-HT agonist or antagonist to a mammal afflicted with pruritus. The 5-HT ligands may, for example, be selected from the group consisting of 5-$HT_1$, 5-$HT_2$, 5-$HT_3$, and 5-$HT_4$ agonists, partial agonists and antagonists.

16 Claims, No Drawings

USE OF 5-HT LIGANDS AS ANTI-PRURITIC AGENTS

FIELD OF THE INVENTION

The present invention relates to methods and means for treating pruritus. More particularly, this invention concerns the use of 5-HT receptor binding agents in the treatment of pruritus.

BACKGROUND OF THE INVENTION

Itch, or pruritus, is a common and distressing symptom in a variety of diseases. Pruritus typically occurs in peripheral diseases such as allergic rhinitis, hemorrhoids, and dermatoses of fungal, allergic and non-allergic origin. Itching can also be a major symptom of certain systemic diseases such as Hodgkin's disease, chronic renal failure, polycythema vera, hyperthyroidism and cholestasis [see for example, Herndon, J. H., Jr., *Int. J. Derm.*, 14, 456–484 (1975); Winkelman, R. K., *Med. Clins. N. Am.*, 66, 1119–1133 (1982)]. The clinical importance of pruritus is undeniable but research efforts in this area have been modest, to a great extent owing to the absence of established, specific experimental models of the itch sensation/response, especially in preclinical research where animals that cannot communicate the nature of the sensation they are experiencing must be used.

The intracutaneous injection of histamine or proteases elicit itch, and this has been used as an experimental model for itch studies [Cormia, R. E., *J. Invent. Derm.* (Chicago), 76, 296–323 (1957)]. It was, therefore, postulated that these agents are involved as mediators in various itching conditions. However it has become apparent that central transmission of the itch sensation involves more than histamine or proteases. Since histamine was believed to be the primary mediator of the itch sensation, conventional itch therapy involves $H_1$-antihistamines as a first-line medication. However, antihistamines have no general anti-pruritic effect, in many instances they are either ineffective or only partially effective. The physician is often obliged to resort to glucocorticoids to relieve pruritus, but the potential undesirable side effects from glucocorticoid therapy are of great concern. Glucocorticoids cause skin atrophy and are absorbed systemically to cause Cushings disease-like effects. It has been concluded that although histamine is undoubtedly a potent pruritogen, there are other mechanisms operative in the clinically encountered spectrum of diseases where itch is a major symptom.

One important aspect in pruritus research is finding an accurate model of itch which allows reproducible determinations of pruritogenic compounds as well as compounds which alleviate itch. The itch sensation and nociception (perception of pain or injurious stimuli) had been believed to be somewhat similar in terms of neural transmission and central nervous system mediation. However a recent review article by Wahlgren, C.-F., *Allergy*, 47, pp. 65–75 (1992) on itching states:

Today's knowledge of the pathophysiology of itching is based on studies of human subjects, as no research models for the investigation of itching in animals are established. Although scratching often occurs in animals, there is no definite proof that it always reflects itching. The highly subjective nature of pruritus makes it an intricate task for the investigator to evaluate. To circumvent the problem of measuring such a subjective symptom, some investigators have developed methods for measurement of scratching, as this is the objective correlate to itching.

Itching can be elicited by chemical, electrical, mechanical and thermal stimulation. No morphological structure has been identified as a specific receptor for the itch sensation, but it is assumed that itch receptors are linked to the free nerve endings of C-fibers close to the dermo-epidermal junction. The impulses set up in the thin, non-myelinated, slowly conducting C-fibers enter the spinal cord via the dorsal horn, then ascend in the contralateral spinothalmic tract, pass via the thalamus and end in the somatosensory cortex of the post-central gyrus. Itching and pain are related phenomena, and it was previously believed that itching was equal to sub-threshold pain, i.e. with increased activity in the C-fibers the perceived sensation changed from itching to pain. Today, itching and pain are considered as two separate sensory modalities. The reasons for this are: a) that both sensations can be felt simultaneously, b) that if the epidermis is removed itching cannot be elicited, whereas pain can still be provoked, c) that itching and pain evoke different motor responses (scratching and withdrawal, respectively), d) that opioids provoke itching, but relieve pain, and e) recent neurophysiological findings. By inserting micro-electrodes percutaneously in peripheral C-fibers of conscious volunteers, Torebjork & Ochoa [*Soc. Neurosci. Abstr.*, 7 p.228 (1981)] showed that electrical stimulation of some C-fibers provoked itching, whereas stimulation of other C-fibers induced pain. If itching was induced, increased stimulation frequency gave an increased itch intensity, but itching never changed to pain. Further studies, where pruritus was provoked by electrical stimulation or histamine iontophoresis, have confirmed this.

The central mechanisms involved in the modulation, interpretation and processing of pruritus are completely unknown, *but undoubtedly the central nervous system has a great influence on the perception of itching.* For example, emotional stress or anxiety can aggravate pruritus, whereas distraction can relieve it. [italics added]

Thus the state of the art has been shifted to separate nonciceptive neural stimulation a part from transmission of the pruritic sensation.

A number of articles have published in the scientific literature on the scratching behavior induced by substance P (a decapeptide, also known as Neurokinin P) by intrathecal (spinal) or intracerebral administration. It is now generally acknowledged that the reciprocal hind limb scratching directed towards the sides of the upper body and the jaw areas after Substance P (or other stimulatory agent) injection is a response to perceived pain, or is alternately an efferent motor response to receptor-based stimulation. Some of the scratching responses are described as non-purposeful or stereotyped movements, indicating that they are not necessarily in response to any perceived sensation at all, either nociceptive or pruritic in origin, but rather result from stimulation of motorneurones that innervate the hind limb muscles. Licking and biting behavior is also manifested with intrathecal or intracerebral injection of substance P. See, for example, Hylden, J. L. K., et al., *Brain Research*, 217, pp. 212–215 (1981), Piercey, M. F., *Brain Research*, 210, pp. 407–412 (1981), Hylden, J. L. K. and Wilcox, G. L., *Journal of Pharmacology and Experimental Therapeutics*, 226(2), pp. 398–404, (1983), and Meisenberg, G. and Simmons, W. H., *Peptides*, 7, pp. 557–561 (1986).

In the present invention, the inventor has taken great pains to significantly link animal scratching behavior with a clinically known syndrome of itch, i.e. experimental allergic conjunctivitis. The establishment of this animal model of clinically encountered pruritus has also been disclosed in co-pending U.S. application Ser. No. 07/837,568, commonly assigned by the same inventor, and is incorporated herein by reference in its entirety. A number of independent lines of evidence indicate that the itch-scratch response (ISR) to substances administered to the ocular surface reflects a behavioral response to the itch sensation. These can be enumerated as follows: 1) itch-scratch can be elicited by topical administration of antigen to the eyes of presensitized guinea pigs, closely mimicking the situation encountered in allergic conjunctivitis patients; 2) itch-scratch responses occur as part of a typical response to allergic provocation that includes redness, swelling, and leukocyte infiltration into the conjunctiva, which again closely mimics the situation encountered in allergic conjunctivitis patients; 3) histamine, a well-characterized benchmark pruritogen, potently elicits itch-scratch episodes directed to the conjunctiva; 4) drugs known to be of benefit in treating allergic conjunctivitis patients, such as pyrilamine and ketorolac, reduced the ocular itch-scratch episodes associated with allergic provocation in this model; 5) the scratching is entirely and specifically directed towards the afflicted area, i.e. the conjunctiva; 6) the animals appear to exert conscious control over itch-scratch responses, which are interrupted by external sensory stimuli; 7) painful stimuli and foreign bodies do not elicit itch-scratch responses.

The pharmacology of systemic 5-HT analog effects on the itch-scratch responses associated with experimental allergic conjunctivitis is very different from that associated with intrathecal substance P induced hind limb scratching. See, for example: Alhaider, A. A., et al., *Eur. J. Pharmacol.*, 249 (2), pp. 151–160 (1993). All 5-HT ligands, either agonists or antagonists, tested in the reduction of the present invention to practice inhibited the itch-scratch response associated with experimental conjunctival allergy. In Alhaider, intrathecal 5-methoxy-N,N-dimethyl tryptamine (5-MeO-DMT), a $5\text{-HT}_{1A}/5\text{-HT}_{1B}$ receptor agonist enhanced intrathecal substance P induced scratching. This is in complete contrast to the inhibitory effect achieved with $5\text{-HT}_{1A}$ and $5\text{-HT}_{1B}$ agonists (8-OH-DPAT, CGS 12066B) in the allergic conjunctival itching model. Furthermore, 5-MeO-DMT enhancement of intrathecal substance P induced scratching was inhibited by MDL 72222 and spirotraxine, but not ketanserin. This differs from the itch-scratch response associated with experimental allergic conjunctivitis in that ketanserin is also inhibitory in this model. These findings further support the literature in distinguishing nociception from pruritus.

Another study by Berendsen and Broekkamp [Berendsen, H. H. G. and Broekkamp, C. L. E., *Eur. J. Pharmacol.*, 194, pp. 201–208 (1991) sought to identify the pharmacological characteristics of hind limb scratching induced by serotonergic compounds. The authors hypothesized that 5-MeO-DMT (and other 5-HT analogs as well as 5-HT itself) induced scratching in the rat after subcutaneous injection which was mediated by serotonergic receptors. The authors concluded that the hind limb scratching induced by 5-HT analogs is probably mediated by binding to the $5\text{-HT}_{1D}$ receptor outside the blood-brain barrier. Other 5-HT ligands were found to potentiate the hind limb scratching induced by 5-MeO-DMT, in particular they note that the $5\text{-HT}_{1D}$ agonist methiothepin had this effect. Other 5-HT ligands were found to attenuate scratching behavior, and it was also noted that $\alpha_2$ antagonists could also attenuate hind limb scratching. Nowhere in the article do the authors state or infer that hind-limb scratching elicited in this study is symptomatic or indicative of itch (or pruritus).

5-Hydroxytryptamine (5-HT), also called serotonin, is a neurotransmitter present in most organisms ranging from humans to species with quite primitive nervous systems. 5-HT elicits a wide variety of behaviors such as aggressive postures in lobsters, feeding and learning in snails, locomotion in lampreys and affects sleep and appetite in mammals. This appearance across species and even across tissues within species can be explained both by the wide distribution of 5-HT and the multiplicity of 5-HT receptors.

Several distinct 5-hydroxytryptamine (5-HT) subtypes, grouped in four main classes of $5\text{-HT}_1$, $5\text{-HT}_2$, $5\text{-HT}_3$, and $5\text{-HT}_4$ receptors, are known to mediate the physiological effects of the neurotransmitter. Since the late 1970's, binding studies have led the way in the initial identification of distinct $5\text{-HT}_1$ and $5\text{-HT}_2$ receptors, and the subsequent subdivision of $5\text{-HT}_1$ receptors into $5\text{-HT}_{1A}$, $5\text{-HT}_{1B}$, $5\text{-HT}_{1C}$ (recently reclassified as $5\text{-HT}_{2C}$), $5\text{-HT}_{1D}$, $5\text{-HT}_{1E}$ binding sites. For a discussion of receptor subtypes and classification see Humphrey, P. P. A., et al., *TiPS*, 14, (June) pp. 233–236 (1993).

Examples of 5-HT receptor agents that have found clinical or pharmacological use are: buspirone, a $5\text{-HT}_{1A}$ partial agonist that is used as an anxiolytic; ketanserin, a $5\text{-HT}_2$ antagonist (also at $\alpha_1$ receptors) is used as an antihypertensive agent; quipazine, a $5\text{-HT}_3$ agonist has found use as an antidepressant; and sumatriptan a $5\text{-HT}_{1D}$ agonist is used in treating migraine headaches.

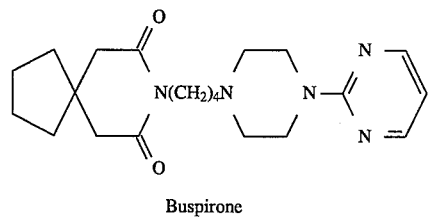

Buspirone

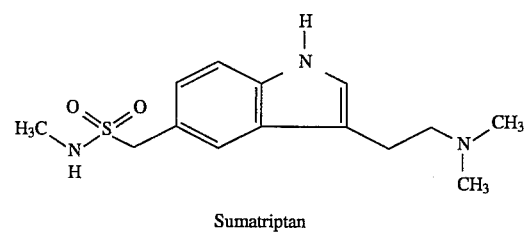

Sumatriptan

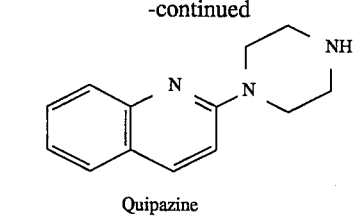

Quipazine

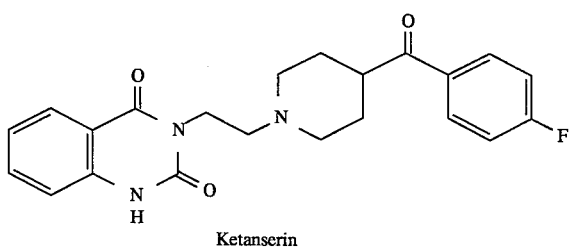

Ketanserin

For a review of 5-HT receptor agonists and antagonists and associated biochemical and pharmacological aspects see Middlemiss, D. N. and Tricklebank, M. D., *Neurosciences and Biobehavioral Reviews*, 16, pp. 75–82 (1992).

Another review article on 5-HT receptors by R. Hen [*TiPS*, 13, (April) pp.160–165 (1992) concludes:

5-HT and 5-HT receptors appeared early in evolution before the separation of vertebrates and invertebrates. This may be related to the fact that in most species 5-HT is involved in the modulation of neuronal activity, a feature that is likely to be required even in primitive organisms in order to adapt to changes in the environment.

Most 5-HT receptors belong to the G-protein coupled family of receptors, the specificity of which involves several parameters: affinity for 5-HT, coupling with different second messenger systems, expression patterns and subcellular localization. The expression pattern of these receptors is often complex and not limited to a particular organ, suggesting that their role is not confined to a particular physiological function but rather to modulation of multiple circuits in order to influence various components of complex behaviors such as aggression or escape.

The review by Middlemiss and Tricklebank (vide supra) concludes:

Functional and receptor binding studies of the actions of 5-HT receptor agonists and antagonists have led to claims of no less than eleven subtypes of 5-HT receptor. Of these, five have been positively differentiated by receptor cloning and purification. Attempts to identify receptor selective drugs have so far yielded selective agonists for $5\text{-HT}_{1A}$, $5\text{-HT}_{1B}$, and $5\text{-HTS}_3$ and selective antagonists for $5\text{-HT}_2$ and $5\text{-HT}_3$ receptors. Clearly 5-HT receptor pharmacology is in its infancy.

SUMMARY OF THE INVENTION

The present invention is based on the finding that 5-HT receptor ligands are useful in treating experimental models of clinically encountered pruritus (itch). A ligand as used in this specification is a compound which is capable of binding with some selectivity to one or more of the 5-HT receptor sites. Systemic administration of 5-HT agonists and antagonists causes a reduction in the number of itch-scratch responses to an ocular challenge by allergenic antigens.

In one aspect, the present invention relates to a method for treating pruritus by administering a therapeutically effective amount of a 5-HT agonist or antagonist to a mammal afflicted with pruritus. The 5-HT ligands may, for example, be selected from the group consisting of $5\text{-HT}_1$, $5\text{-HT}_2$, $5\text{-HT}_3$, and $5\text{-HT}_4$ agonists, partial agonists and antagonists.

Further aspects of the invention will become apparent upon a close reading of the specification.

DETAILED DESCRIPTION OF THE INVENTION

5-HT is an endogenous compound that serves as a neurotransmitter, and has a role in both the central and peripheral transmission of neural signals. At present there have been identified or proposed 11 types and subtypes of 5-HT receptors. The classification of characterized receptors is made as follows: $5\text{-HT}_{1A}$, $5\text{-HT}_{1B}$, $5\text{-HT}_{1D}$, $5\text{-HT}_2$, $5\text{-HT}_{2C}$, $5\text{-HT}_3$ and $5\text{-HT}_4$, some of these subtypes are found in some species and not others. Some receptors are homologous across species, but not all.

Additionally, except for the 5-HT3 receptor which is a member of the ligand-gated ion channel family, all the cloned 5-HT receptors belong to the superfamily of receptors that couple with G proteins. $5\text{-HT}_{1A}$, $5\text{-HT}_{1B}$, $5\text{-HT}_{1D}$ receptors inhibit adenylyl cyclase while the $5\text{-HT}_2$, $5\text{-HT}_{2C}$ activate phospholipase C to produce inositol phosphates. The $5\text{-HT}_4$ receptor is positively coupled to adenylyl cyclase. The 5-HT3 receptor is associated with an ion channel that mediates fast depolarizing neural responses by opening monovalent cation selective membrane channels.

It has been unexpectedly found that administration of either agonists or antagonists of 5-HT receptors, i.e. 5-HT ligands, in more general terminology, are useful in relieving itch associated with experimental allergy. Although it is not known definitively and applicants do not wish to be bound by one particular theory, it appears that 5-HT ligands suppress the central transmission of peripherally derived neuronal signals that relay the itch sensation. 5-HT itself has no effect in eliciting an itch response when locally applied, and is not known as a pruritic mediator (pruritogen), in contrast to such compounds as histamine and PAF (platelet activating factor).

It has also been found that 5-HT ligands can block histamine and PAF induced itching, which demonstrates that these compounds find use in treating both allergic and non-allergic induced itch.

In applying the compounds of this invention to treatment of pruritic conditions, administration of the active compounds and salts described herein can be given via any of the accepted modes of administration for agents which affect the central nervous system including oral, parenteral, and otherwise systemic routes of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms, or in sustained or controlled release dosage forms for the prolonged administration of the compound at a predetermined rate. The composition will typically include a conventional pharmaceutical carrier or excipient and the active compound, a 5-HT ligand, and may additionally include other medicinal agents, pharmaceutical agents, carriers, adjuvants, etc.

The amount of active compound will of course, be dependent on the subject being treated, the severity of the affliction, the manner of administration, and the judgment of the prescribing physician. However, an effective dosage is in the range of 0.01 to 10 mg/kg/day, preferably 0.1 to 2.5 mg/kg/day.

For solid compositions, conventional non-toxic carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol as a carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like to thereby form a solution or suspension. If desired, the pharmaceutical composition to be administered may also contain minor amounts of non-toxic auxiliary pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or composition containing active ingredient or its salts in the range of 0.25 to 95% with the balance made up from non-toxic carrier may be prepared.

For oral administration, a pharmaceutically acceptable non-toxic composition is formed by the incorporation of any of the normally employed excipients, and may contain 1%–95% active ingredient, preferably 5%–50%.

Parenteral administration is generally characterized by injection, whether subcutaneously, intramuscularly, or intravenously. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, triethanolamine oleate, etc.

The percentage of active compound contained in such parenteral compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

A more complete appreciation of the invention may be obtained from the following example. As a means of providing an atraumatic experimental model of itching, the conjunctiva was used as a convenient tissue site. Pruritogenic agents may be administered to the conjunctiva without the need to traumatize the tissue by injection or scarification. The itch sensation is elicited peripherally by local, atraumatic application of the pruritogen to the conjunctiva which is a convenient site for modeling diseases where itching is a major symptom. In animals presensitized to a particular antigen, subsequent topical challenge with that antigen results in conjunctival itching. This may be considered an experimental model of itching which has general relevance to clinically encountered pruritus. In the studies described herein, chicken ovalbumin was used as an antigenic substance and the ability of 5-HT ligand pretreatment to block the itching response was examined.

EXAMPLE 1

Albino guinea pigs (Dunkin-Hartley strain, either sex) were used. The animals were sensitized to chicken ovalbumin (Sigma, St. Louis, Mo.) and were housed 2–3 per cage. The cages were of standard dimension [24×18×14 in] with metal grid floors. A period of at least one month was allowed for the animals to become accustomed to their surroundings. Temperature and humidity were carefully controlled at $75°\pm2°$ F. and $50\pm5\%$, respectively.

In order to obtain the maximal number of itch-scratch responses (ISR) per unit time, it was found important to keep animals in groups of 2–3 and in their normal surroundings during the stimulation. The studies involved opening the front access doors to 180° to allow uninterrupted observation and to prevent access to the door-mounted feed hopper. Each animal was taken in turn from the cage to administer the stimulus and then immediately replaced in the cage. Drugs were injected subcutaneously in the scruff of the neck in a volume of 1 mg/kg or in some cases 10 mg/kg body weight. In all experiments the number of itch-scratch responses (ISR) were observed and recorded over a 15 min period beginning at the time when the animal was returned to its cage. The scratching episodes involved successive hind limb movements of rapid frequency such that recording each movement was well beyond the capability of human hand-eye coordination. The ISR was defined as an uninterrupted cluster of rapid hind limb movements which were precisely directed to the ocular surface that received the stimulus. Thus, each scratch episode typically comprised several hind limb movements: a single hind limb movement to the ocular surface was rare and such occurrences were not designated as an itch-scratch response. Front limb responses were also excluded since preliminary observation revealed that such movements often occurred as part of grooming.

Table 1 summarizes the testing of eight different 5-HT ligands for use in pretreatment of itching response to antigenic challenge. The effects of a variety of 5-HT ligands are compared to vehicle control therein. A statistically significant reduction in the ocular surface itching was achieved with the 5-HT ligands employed. The 5-HT uptake inhibitor 6-nitroquipazine was, however, inactive. This finding indicates that specific interaction with a 5-HT receptor is required to obtain the anti-pruritic effect. All drugs were administered as a 30 minute pretreatment.

TABLE 1

Effect of 5-HT on Itch Responses Associated with Allergic Conjunctivitis

| DRUG | PHARMACO-LOGICAL CLASS | DOSE | # ITCH-SCRATCH EPISODES |
|---|---|---|---|
| α-Methyl-serotonin maleate | $5HT_2$ Agonist | 1 mg/kg | $5.2 \pm 1.1$ |
| Vehicle | | | $11.8 \pm 1.8**$ |
| Spiroxatrine | $5HT_{1A}$ Antagonist | 1 mg/kg | $5.0 \pm 0.8**$ |
| Spiroxatrine | | 10 mg/kg | $1.9 \pm 0.4**$ |
| Vehicle | | | $8.25 \pm 0.9$ |
| Ketanserin | $5HT_2/$ | 1 mg/kg | $5.3 \pm 0.7**$ |

TABLE 1-continued

Effect of 5-HT on Itch Responses Associated with Allergic Conjunctivitis

| DRUG | PHARMACO-LOGICAL CLASS | DOSE | # ITCH-SCRATCH EPISODES |
|---|---|---|---|
| Ketanserin | 5HT$_{1A}$ Antagonist | 10 mg/kg | 1.8 ± 0.6** |
| Vehicle | | | 8.6 ± 0.9 |
| Quipazine | 5HT$_3$ Agonist | 1 mg/kg | 3.7 ± 0.5** |
| Vehicle | | | 8.4 ± 0.9 |
| Quipazine | | 10 mg/kg | 0.9 ± 0.7** |
| Vehicle | | | 8.1 ± 0.7 |
| MDL 72222 | 5HT$_3$ Antagonist | 1 mg/kg | 4.7 ± 0.6** |
| Vehicle | | | 8.4 ± 0.9 |
| MDL 72222 | | 10 mg/kg | 2.1 ± 0.5** |
| Vehicle | | | 8.1 ± 0.7 |
| 2-Methyl-serotonin | 5HT$_3$ Agonist | 1 mg/kg | 2.43 ± 0.4** |
| Vehicle | | | 7.4 ± 0.5 |
| 2-Methyl-serotonin | | 10 mg/kg | 1.7 ± 0.6** |
| Vehicle | | | 5.4 ± 0.7 |
| 8-OH-DPAT | 5HT$_{1A}$ Agonist | 1 mg/kg | 5.9 ± 1.1** |
| Vehicle | | | 11.8 ± 1.4 |
| CGS 12066B | 5HT$_{1B}$ Agonist | 1 mg/kg | 7.9 ± 1.2* |
| Vehicle | | | 11.8 ± 1.4 |
| 6-Nitro-quipazine | 5HT uptake inhibitor | 1 mg/kg | 9.9 ± 0.8 |
| Vehicle | | | 11.8 ± 1.4 |

*p <0.05
**p <0.01 according to Students' non-paired t test [n = 6–12]

The 5-HT ligands listed in table 1 above are also identified by the following chemical nomenclature and CAS Registry numbers: α-methylserotonin is 3-(2-aminopropyl)-1H-Indol-5-ol (CAS 304-52-9); spiroxatrine is 8-(1,4-benzodioxan-2-ylmethyl)-1-phenyl-1,3,8-trianaspiro[4,5]decane-4-one (CAS 1054-88-2); ketanserin is 3-[2-[4-(p-fluorobenzoyl)- 1-piperidinyl]ethyl]-2,4(1H,3H)quinazolinedione (CAS 74050-98-9); quipazine is 2-(1-piperazinyl)-quinoline (CAS 4774-24-7); MDL 72222 is endo-8-methyl-8-azabicyclo[3.2.1]oct-3-yl-3,5-dichlorobenzoate (CAS 40796-97-2); 2-methylserotonin is 3-(2-aminoethyl)- 2-methyl-1H-indol-5-ol (CAS 78263-90-8);8-OH-DPAT is 7-(dipropylamino)- 5,6,7,8-tetrahydro-1-naphthalenol (CAS 78950-78-4); and CGS 12066B is 4-(4-methyl-1-piperazinyl)-7-(trifluoromethyl)pyrrolo[1,2-a]quinoxaline (CAS 109028-09-3).

It is understood that this invention may be embodied in a variety of forms without departing from the spirit or essential characteristics of this disclosure. Thus, however detailed the foregoing may appear in text, it should not be construed as limiting the overall scope hereof; rather, the ambit of the present invention is to be governed only by the lawful construction of the appended claims.

We claim:

1. A method for treating pruritus which comprises administering a therapeutically effective amount of a 5-HT ligand selected from the group consisting of 5-HT$_{1,2,3}$ and $_4$ agonists and all subtypes thereof; 5-HT$_1$ and $_2$ antagonists and all subtypes thereof; and a pharmaceutically acceptable salt or ester thereof, to a mammal afflicted with pruritus.

2. The method of claim 1, wherein said 5-HT ligand is a 5-HT agonist.

3. The method of claim 1, wherein said 5-HT ligand is a 5-HT$_{1A,1B}$, or $_{1D}$ antagonist.

4. The method of claim 1, wherein said 5-HT ligand is a 5-HT$_2$, or 5-HT$_{2C}$ antagonist.

5. The method of claim 1, wherein said 5-HT ligand is a 5-HT$_3$ agonist.

6. The method of claim 1, wherein said 5-HT ligand is a 5-HT$_4$ agonist.

7. The method of claim 1, wherein said 5-HT ligand is selected from the group consisting of α-methylserotonin, spirotraxine, ketanserin, quipazine, 2-methylserotonin, 8-OH-DPAT and CGS 12066B.

8. The method of claim 1 wherein said 5-HT ligand or salt or ester is administered orally.

9. A method of treating pruritus in a mammal afflicted with allergic conjunctivitis which comprises administering systematically a therapeutically effective amount of a 5-HT ligand selected from the group consisting of 5-HT$_{1,2,3}$ and $_4$ agonists and all subtypes thereof; 5-HT$_1$ and $_2$ antagonists and all subtypes thereof; and a pharmaceutically acceptable salt or ester thereof.

10. The method of claim 9, wherein said 5-HT ligand is a 5-HT agonist.

11. The method of claim 9, wherein said 5-HT ligand is a 5-HT$_{1A,1B}$, or $_{1D}$ antagonist.

12. The method of claim 9, wherein said 5-HT ligand is a 5-HT$_2$, or 5-HT$_{2C}$ antagonist.

13. The method of claim 9, wherein said 5-HT ligand is a 5-HT$_3$ agonist.

14. The method of claim 9, wherein said 5-HT ligand is a 5-HT$_4$ agonist.

15. The method of claim 11, wherein said 5-HT ligand is selected from the group consisting of α-methylserotonin, spirotraxine, ketanserin, quipazine, 2-methylserotonin, 8-OH-DPAT and CGS 12066B.

16. The method of claim 9, wherein said 5-HT ligand or salt or ester is administered orally.

* * * * *

UNITED STATES PATENT AND TRADEMARK OFFICE
CERTIFICATE OF CORRECTION

PATENT NO. : 5,521,183

DATED : May 28, 1996

INVENTOR(S) : Woodward et al

It is certified that error appears in the above-identified patent and that said Letters Patent is hereby corrected as shown below:

Column 5, line 52; delete "$5-HTS_3$" and insert in place thereof --$5-HT_3$--

Signed and Sealed this

Twentieth Day of August, 1996

Attest:

BRUCE LEHMAN

Attesting Officer

Commissioner of Patents and Trademarks